(12) United States Patent
Baranyai et al.

(10) Patent No.: US 12,269,790 B1
(45) Date of Patent: Apr. 8, 2025

(54) PROCESS FOR THE PREPARATION OF 2,4,6-TRIIODOPHENOL DERIVATIVES

(71) Applicant: BRACCO IMAGING S.P.A., Milan (IT)

(72) Inventors: Zsolt Baranyai, Trieste (IT); Nicol Guidolin, Trieste (IT); Federica Lazzari, Novara (IT); Fulvio Uggeri, Codogno (IT)

(73) Assignee: BRACCO IMAGING S.P.A., Milan (IT)

( * ) Notice: Subject to any disclaimer, the term of this patent is extended or adjusted under 35 U.S.C. 154(b) by 0 days.

(21) Appl. No.: 18/860,494

(22) PCT Filed: Apr. 28, 2023

(86) PCT No.: PCT/EP2023/061272
§ 371 (c)(1),
(2) Date: Oct. 25, 2024

(87) PCT Pub. No.: WO2023/209165
PCT Pub. Date: Nov. 2, 2023

(30) Foreign Application Priority Data

Apr. 29, 2022 (EP) .................................. 22170765

(51) Int. Cl.
*C07C 235/48* (2006.01)
(52) U.S. Cl.
CPC .................................. *C07C 235/48* (2013.01)
(58) Field of Classification Search
None
See application file for complete search history.

(56) References Cited

U.S. PATENT DOCUMENTS 3,914,294 A   10/1975   Bernstein et al.

FOREIGN PATENT DOCUMENTS

| WO | 8809328 A1 | 12/1988 |
|---|---|---|
| WO | 9414478 A1 | 7/1994 |
| WO | 9705097 A1 | 2/1997 |
| WO | 0032561 A1 | 6/2000 |
| WO | 2009103666 A2 | 8/2009 |
| WO | 2011154500 A1 | 12/2011 |

OTHER PUBLICATIONS

Greene, T.W. et al. (eds.), "Protection for the Amino Group," Chapter 7, pp. 494-653, In: Protective Groups in Organic Synthesis, John Wiley & Sons, Inc. (1999).
International Search Report and Written Opinion for PCT/EP2023/061272, mailed Jul. 31, 2023.
Joshi, S.N. et al. "Regioselective iodination of chlorinated aromatic compounds using silver salts," Tetrahedron, 67:7461-7469 (2011).
Yusubov, M. et al. "Solvent-Free Iodination of Arenes using Iodine-Silver Nitrate Combination," Synthetic Communications, 37:1259-1265 (2007).

*Primary Examiner* — Sudhakar Katakam
*Assistant Examiner* — Jennifer C Sawyer
(74) *Attorney, Agent, or Firm* — VIVICAR Law, PLLC

(57) ABSTRACT

The invention relates to a process for the preparation of a 2,4,6-triiodo-phenol derivative of formula (II), which is useful as an intermediate for the synthesis of conventional X-ray contrast agents, said process comprising the tri-iodination of the correspondent phenol derivative of said 2,4,6-triiodo-phenol derivative by means of an iodinating system comprising $I_2$ and an oxide or a salt of an element of group 11 of the periodic table.

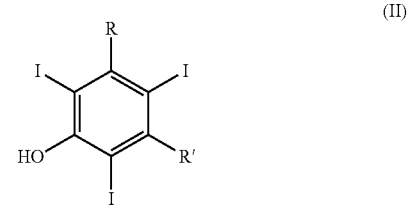

(II)

20 Claims, 1 Drawing Sheet

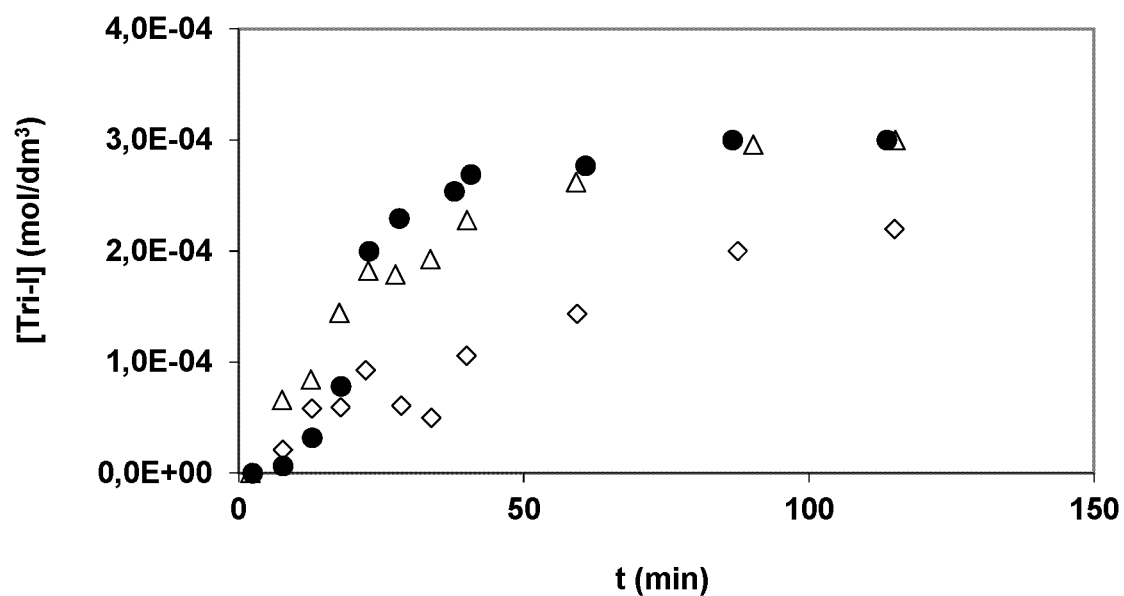

PROCESS FOR THE PREPARATION OF 2,4,6-TRIIODOPHENOL DERIVATIVES

CROSS-REFERENCE TO RELATED APPLICATIONS

This application is the national stage application of corresponding international application number PCT/EP2023/061272, filed Apr. 28, 2023, which claims priority to and the benefit of European application no. 22170765.6, filed Apr. 29, 2022, which is hereby incorporated by reference in its entirety.

TECHNICAL FIELD

The invention relates to a process for the preparation of a 2,4,6-triiodo-phenol derivative comprising the tri-iodination of a phenol derivative. The 2,4,6-triiodo-phenol is an intermediate for the synthesis of conventional X-ray contrast agents, such as iomeprol.

BACKGROUND OF THE INVENTION

Non-ionic X-ray contrast agents are a well-known class of contrast agents characterized by its triiodinated aromatic structure. Suitable examples of the same include diatrizoate, iothalamate, ioxithalamate, metrizoate, iohexol, iomeprol, iopamidol, iopentol, iopromide, ioversol, ioxilan, iosarcol, iogulamide, acetrizoate and iodamide, which are monomeric; and ioxaglate, iodixanol, iotrolan, iotasul, iodipamide, iocarmate, iodoxamate, iotroxate and iotrolan, which are dimeric. Other examples of triiodinated aromatic compounds useful as non-ionic X-ray contrast agents are described, for instance, in WO 94/14478.

Several multistep syntheses are currently employed for the preparation of the triiodinated aromatic compounds above. A particularly important step of these multistep synthesis is the iodination of a 3,5-disubstituted phenol derivative to obtain a 2,4,6-triiodo-3,5-disubstituted phenol derivative. Indeed, the latter can then be reacted with an amide, and finally subjected to Smile's rearrangement (for instance, as disclosed in WO 88/09328 and in WO 97/05097), to obtain the final triiodinated aromatic compound useful in X-ray diagnosis. This general process is well known and is disclosed, for example, in WO 00/32561.

The iodination step of a phenol derivative for the preparation of the 2,4,6-triiodo-phenol derivative is conventionally carried out using ICl in concentrated hydrochloric acid (HCl), or the analogues salts of ICl, such as KICl$_2$ and NaICl$_2$, in aqueous solution, as disclosed for example in WO 00/32561 and U.S. Pat. No. 3,914,294.

However, ICl and analogues thereof are strong corrosive acids with limited storage life and stability, which generate iodine vapours even at room temperature. ICl can be generally stabilized with high quantity of HCl, which in turn must be neutralized prior to waste treatment, leading thus to an increase in operation time, waste volumes and costs. Furthermore, when using ICl and analogues thereof, there could be reduction of the quality of the final product (in the terms of yield and purity), because chlorine gas that generate can in turn react by aromatic electrophilic substitution with the phenol substrate, thus leading to the undesired formation of chlorinated by-products.

Therefore, attempts have been made to carry out the iodination step avoiding the use of ICl and analogues thereof, for example using iodine (I$_2$) as the iodinating reagent.

WO 2009/103666 discloses the synthesis of triiodinated aromatic compounds by electrochemical triioduration of 3,5-disubstituted phenol derivatives. The triiodination reaction carried out in WO 2009/103666 requires stepwise addition of the substrate, reaction times higher than 2 hours, and heating the reaction mixture at reflux.

WO 2011/154500 discloses the in-situ generation of the iodinating species, from iodine I$_2$ and a suitable oxidant, typically HIO$_3$, to prepare iodinated phenols, by heating the reaction mixture to 60° C. It should be noted that heating at 60° C. or higher during the iodination reaction, in particular when the substrate contains hydrolysable moieties, such as the amide moieties that are present in iomeprol intermediates, leads to partial hydrolyzation of such moieties, and consequently to a reduction of the overall yield and to the generation of by-products.

Joshi S. N. et al. (Tetrahedron (2011), 67, 7461-7469) discloses iodination of dichlorinated phenols in an organic solvent with AgX/I$_2$, where X is selected from —SO$_4$ and non-coordinating anions such as BF$_4^-$ and PF$_6^-$. This paper further discloses that silver salts activate I$_2$ by forming insoluble silver iodide, thus generating an electrophilic iodine species. However, even though regioselective iodination is achieved, the iodination disclosed in Joshi S. N. et al. has many disadvantages, such as long reaction times and the medium in which is carried out, namely dichloromethane, which is known to be highly volatile and not ideal from a safety-standpoint.

Yusubov M. et al. (Synthetic Communications (2007), 37, 1259-1265) discloses the solvent-free monoiodination of nitrophenols and other aromatic compounds by I$_2$/AgNO$_3$, obtained after grinding for 10-30 min in an agate mortar, with a yield ranging from 54 to 90%. This iodination takes place in a short amount of time in the solid-state, or as a slurry formed by the addition of few drops of acetic acid. However, the reaction is not complete as yields do not exceed 90%. Moreover, carrying out the reaction in a solid-state or slurry is not advantageous from an industrial development standpoint.

Applicant has now found a new iodination process that allows to carry out the iodination of the substrate with good reaction times and good yields, advantageously in mild reaction conditions.

SUMMARY OF THE INVENTION

The present invention relates to a process for the tri-iodination of a phenol of formula (I), or a salt thereof, to obtain the 2,4,6-triiodophenol of formula (II), or a salt thereof

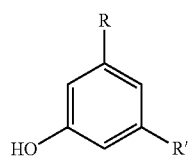

Formula (I)

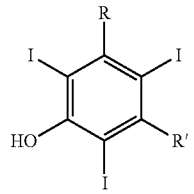

Formula (II)

as set out in the claims.

The process of the invention provides several advantages by virtue of its iodinating system, in particular when the latter comprises silver and copper, as it allows carrying out a tri-iodination reaction that does not generate, at least to a significant extent, side-products deriving from either the partial iodination of the aromatic ring or any other impurity. Moreover, the process of the invention provides high yields and substantially complete conversion of the phenol to the 2,4,6-triiodophenol by operating at room temperature and with low reaction times. Furthermore, the process of the invention is advantageously carried out in an aqueous medium, thereby improving the safety and cost-effectiveness of the process of the invention compared to some of the prior art tri-iodination processes.

The embodiments of the present invention are set out in the dependent claims.

FIGURES

FIG. 1 shows, as a function of time, the amount of Compound 2 ("Tri-I") formed during the reaction of:
Example 1 (Comparative) ([Compound 1]=0.3 mM, [I$_2$]=1.1 mM, pH=7.5 and 25° C.) (diamond ◇);
Example 2 ([Compound 1]=0.3 mM, [I$_2$]=1.1 mM, [Ag$_2$O]=0.55 mM, pH=7.5 and 25° C.) (triangle ◇), and
Example 3 ([Compound 1]=0.3 mM, [I$_2$]=1.1 mM, [Cu$^{2+}$]=1.1 mM, [NaHCO$_3$]=0.2 M, pH=7.5 and 25° C.) (circle •).

DETAILED DESCRIPTION OF THE INVENTION

In accordance with a first aspect, the present invention relates to a process for the preparation of a 2,4,6-triiodophenol of formula (II), or a salt thereof,

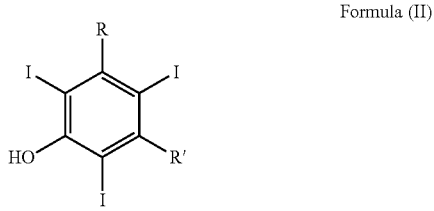

Formula (II)

wherein R and R' represent, independently from one another, a moiety selected from the group consisting of hydrogen, —COOR$_1$, and —CONR$_1$R$_2$;
wherein R$_1$ and R$_2$ represent, independently from one another, hydrogen or a C$_1$-C$_6$ alkyl group, preferably a C$_1$-C$_4$ alkyl group, optionally substituted by one or more groups selected from hydroxyl (—OH), C$_1$-C$_6$ alkoxy, and C$_1$-C$_6$ hydroxyalkoxy;
comprising the following steps:
a) providing a phenol of formula (I), or a salt thereof

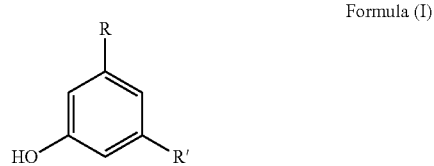

Formula (I)

wherein R and R' have the same meaning provided above;
b) providing an iodinating system comprising I$_2$ and at least an oxide of or a salt of an element of group 11 of the periodic table, preferably of silver or copper, provided that when the element of group 11 is copper, the iodinating system further comprises at least phosphoric acid, carbonic acid, and/or ions thereof;
c) reacting said phenol of step a) and said iodinating system of step b) in an aqueous medium having a pH comprised in the range of 7.0 to 9.0, to obtain the 2,4,6-triiodophenol of formula (II).

Unless otherwise provided, the term "element of group 11" refers to any of the chemical elements of group 11 of the periodic table by modern IUPAC numbering (and is thus a transition metal). The element of group 11 is thus selected from the group consisting of copper (Cu), silver (Ag), gold (Au), and roentgenium (Rg), with silver and copper being particularly preferred.

Unless otherwise provided, the term "oxide of an element of group 11" refers to a metal oxide between the dianion of oxygen O$^{2-}$ and the element of group 11 as above defined, preferably such element being silver or copper. Preferred oxides are thus Ag$_2$O, Cu$_2$O, and CuO, with Ag$_2$O being particularly preferred.

Unless otherwise provided, the term "salt of an element of group 11" refers to a compound consisting of an ionic assembly of the cation of the element of group 11, preferably of a cation of silver or copper, with any anion as counter ion. Preferably, the anion of the salt of an element of group 11 is not a halide, namely is not iodide, bromide, chloride nor fluoride. In other words, the salt of an element of group 11 preferably does not comprise a halide as anion. Preferred anions are phosphate, sulphate, carbonate and nitrate ions, possibly hydrogenated, such as phosphate (PO$_4^{3-}$), monohydrogen phosphate (HPO$_4^{2-}$), dihydrogen phosphate (H$_2$PO$_4^-$), sulfate (SO$_4^{2-}$), bisulfate (HSO$_4^-$), carbonate (CO$_3^{2-}$), bicarbonate (HCO$_3^-$), and nitrate (NO$_3^-$). Accordingly, particularly preferred salts are the salts of silver or copper with an anion selected from the list mentioned above.

Unless otherwise provided, the term "phosphoric acid, carbonic acid, and/or ions thereof" indicates phosphoric acid (H$_3$PO$_4$), carbonic acid (H$_2$CO$_3$), as well as their anions, possibly hydrogenated, namely phosphate (PO$_4^{3-}$), monohydrogen phosphate (HPO$_4^{2-}$), dihydrogen phosphate (H$_2$PO$_4^-$), carbonate (CO$_3^{2-}$), and bicarbonate (HCO$_3^-$). Particularly preferred are ions of phosphoric acid and carbonic acid, such as the ones listed above, and even more preferred is bicarbonate (HCO$_3^-$).

Unless otherwise provided, the term "alkyl" refers to a linear or branched hydrocarbon chain. Accordingly, "C$_1$-C$_6$ alkyl" comprises within its meaning a linear or branched chain comprising from 1 to 6 carbon atoms such as methyl, ethyl, n-propyl, isopropyl, n-butyl, isobutyl, sec-butyl, tert-butyl, n-pentyl, n-hexyl, and the like.

Unless otherwise provided, the term "alkoxy" comprises within its meaning an alkyl chain as above defined further comprising one or more oxygen atoms; examples include, for instance, alkyl-oxy (or -Oalkyl) groups such as methoxy, ethoxy, n-propoxy, isopropoxy and the like, and alkyl-(poly)oxy in which the alkyl chain is interrupted by more than two oxygen atoms.

Unless otherwise provided, the term "hydroxyalkoxy" refers to any of the above alkyloxy residues further comprising one or more hydroxyl (—OH) moieties in the alkyl chain.

Suitable examples of alkoxy or hydroxyalkoxy groups comprise methoxy, ethoxy, n-propoxy, isopropoxy, n-pentoxy, 2-hydroxyethoxy, 2,3-dihydroxypropoxy, 1,3-dihydroxyisopropoxy, and the like.

It has been surprisingly found that the process of the invention allows carrying out a tri-iodination reaction that does not generate, at least to a significant extent, side-products deriving from either the partial iodination of the aromatic ring or any other impurity; that is, substantially no chlorinated by-products are present after the completion of step c) of the process of the invention (in particular when the salt of the element of group 11 does not comprise chloride as anion), and the yield of the triiodinated product is relatively high, typically higher than 90%, even higher than 95% in most cases. Accordingly, and differently from some of the iodination processes of the prior art, the purification of the 2,4,6-triiodophenol obtained according to the process of the invention may be avoided. Indeed, such 2,4,6-triiodophenol already fulfils the analytical specifications for the industrially produced intermediate within the crude solution, and may thus be used as such (namely, without isolating and/or purifying it) in the next reaction steps.

Moreover, the process of the invention provides high yields and substantially complete conversion of the phenol to the 2,4,6-triiodophenol by operating at room temperature and with relatively short reaction times, thus resulting in a very convenient process for industrial applications. Indeed, as showed in the Experimental section below, it has been found that substantially complete tri-iodination (>90% yield) can be achieved after about 45 minutes of reaction time (up to about 80 minutes of reaction time, depending on the iodinating system selected), while the complete reaction can be achieved after about 80 minutes of reaction time (or up to about 100 minutes of reaction time, depending on the iodinating system selected) by operating around room temperature. Operating at room temperature is very advantageous, as it substantially avoids the hydrolyzation of the —$COOR_1$, and —$CONR_1R_2$ moieties that are preferably present in the phenol of formula (I), such hydrolyzation usually occurring at some extent even when operating at temperatures higher than 40° C. Accordingly, the reaction step c) can be carried out by adjusting and/or maintaining the temperature to 40° C. or lower, for example in the range of 15° C. to 35° C., e.g. adjusting and/or maintaining the temperature at 25° C. (room temperature), for a time of for example less than 2 hours, preferably less than 1 hour and 30 min, such as for a time comprised in the range of 30 minutes to 2 hours, preferably of 45 minutes to 1 hour and 30 min.

On the contrary, the triiodination reaction carried out without using the iodinating system as herein disclosed provides lower yields and thus an incomplete reaction when the same reaction conditions are used, as it is demonstrated by means of comparative examples and showed in FIG. 1.

Furthermore, the process of the present invention is advantageously carried out in an aqueous medium. According to the present invention, the term "aqueous medium" refers to a solution or suspension comprising water as solvent or as external phase of the suspension. Preferably, the aqueous medium is substantially free from any organic solvent miscible with water, and thus the aqueous medium is a solution or suspension comprising water as the sole solvent or as the sole external phase of the suspension. Accordingly, the process of the invention allows using a solvent, namely water, which is inexpensive and safe for both the users and the environment.

According to a preferred embodiment of the process of the invention, the iodinating system comprises a silver oxide and/or a salt of copper and 12, provided that when the iodinating system comprises such salt of copper, the iodinating system further comprises at least phosphoric acid, carbonic acid, and/or ions thereof. According to a particularly preferred embodiment, the iodinating system is selected from the group consisting of $Ag_2O/I_2$, $I_2/CuSO_4/NaHCO_3$, and mixtures thereof.

According to a preferred embodiment of the process of the invention, for both formulae (I) and (II), R and R' represent, independently from one another, a —$COOR_1$ or a —$CONR_1R_2$ moiety, preferably a —$CONR_1R_2$, wherein $R_1$ and $R_2$, independently from one another, represent hydrogen or a $C_1$-$C_4$ alkyl group optionally substituted by from one to three hydroxyl (—OH), such as, for instance, 1,3-dihydroxyisopropyl, 2,3-dihydroxypropyl, 1,3-dihydroxy-2-methyl-isopropyl, or 2,3,4-trihydroxybutyl.

Even more preferably, for both formulae (I) and (II), R and R' represent, independently from one another, a moiety selected from: —$CONHCH_3$, —$CONHCH_2$—$CH(OH)$—$CH_2OH$, —$CONHCH(CH_2OH)_2$, and —$CON(CH_3)$—$CH_2$—$CH(OH)$—$CH_2OH$.

According to a most preferred embodiment, the phenol of formula (I) is N,N'-bis[2,3-dihydroxypropyl]-5-hydroxy-benzene-1,3-dicarboxamide (Compound 1), and the 2,4,6-triiodophenol of formula (II) is N,N'-bis[2,3-dihydroxypropyl]-5-hydroxy-2,4,6-triiodobenzene-1,3-dicarboxamide (Compound 2)

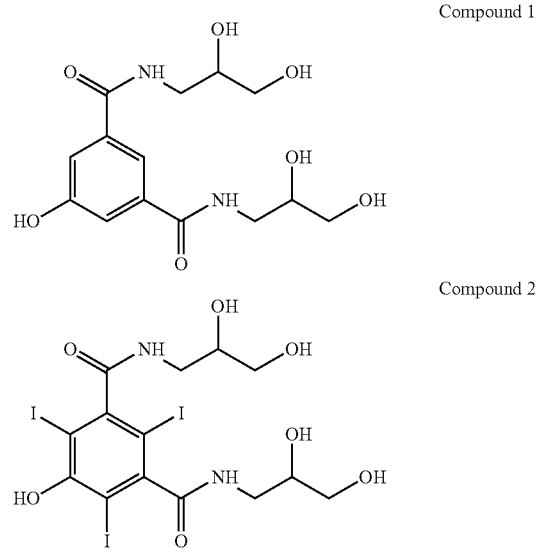

As both R and R' groups do not take direct part to the iodination process, the groups R and R' which may undergo unwanted side reactions could be suitably protected before the iodination step takes place. Protection and subsequent deprotection of the said groups can be accomplished by a variety of methods widely known in the art and conventionally adopted in organic synthesis techniques, for example as disclosed in T. W. Greene, Protective Groups in Organic Synthesis (Wiley, N.Y. 1981).

If needed, the pH of the aqueous medium of step c) of the process of the invention is preferably adjusted and/or maintained to the range provided above, for example by adding a catalytic amount of a suitable base, for instance NaOH or NH$_3$, NH$_3$ being particularly preferred, and/or a catalytic amount of a suitable acid. According to the present invention, the terms "suitable base" and "suitable acid" refer to, respectively, bases and acids that do not take part in the triiodination of the phenol of formula (I), which the person skilled in the art can readily recognize. Suitable bases can be for instance NaOH or NH$_3$, NH$_3$ being particularly preferred, and suitable acids can be for example HClO$_4$. For example, when the iodinating system comprises Ag$_2$O/I$_2$, a base (such as NaOH or NH$_3$) is preferably added (e.g. continuously or step-wise) during step c) to improve the solubilization of Ag$_2$O.

According to a preferred embodiment, the pH of the aqueous medium of step c) of the process of the invention is comprised in the range of 7.5 to 8.0, possibly by adding a catalytic amount of a suitable base, such as the bases provided above, and/or of a suitable acid if needed. According to an embodiment, a base (such as NaOH or NH$_3$) is continuously added during step c) to maintain the pH within the ranges provided above.

Some of the components of the iodinating systems, e.g. Ag$_2$O and I2, might be slightly soluble within the reaction conditions of step c), and accordingly the reaction mixture of step c) might be a suspension.

According to a preferred embodiment, at least step c) is carried out in the dark and/or using non-transparent reactors, i.e. reactors that limit the visible light reaching the reaction mixture, such as stainless steel reactors or reactors covered with tinfoil or with aluminium foil. Indeed, at least step c) is carried out preferably without exposing the reaction mixture to direct sunlight and possibly also to artificial light.

According to a preferred embodiment, step c) of the invention provides for reacting the phenol and the iodinating system, e.g. according to the conditions previously disclosed, in a molar ratio of at least three moles of I$_2$ per mole of phenol. More preferably, the molar ratio of I$_2$ to phenol of the reaction of step c) is comprised in the range of 3:1 to 4:1, even more preferably of 3:1 to 3.5:1.

According to a preferred embodiment, when the iodinating system comprises silver, the molar ratio between I$_2$ and silver (e.g. when present as Ag$_2$O) is at least 4:1, and is preferably comprised in the range of 4:1 to 1:1, more preferably of 3:1 to 1:1, and even more preferably is 2:1. Indeed, it has been found that these ratios allow obtaining complete conversion of the phenols into the 2,4,6-triiodophenol in a short amount of time, typically around 1 hour or less.

According to another preferred embodiment, when the iodinating system comprises copper, the molar ratio between I$_2$ and copper (e.g. when present as CuSO$_4$) is comprised in the range of 1:0.8 to 1:3, and more preferably is 1:1.

It has been found that when copper salt or oxide is comprised in the iodinating system, the reaction of step c) is more effective when at least phosphoric acid, carbonic acid, and/or ions thereof are present as well. The ions of phosphoric acid and carbonic acid can be advantageously provided according to step b) as salt, for example as a sodium or potassium salt, such as Na$_3$PO$_4$, K$_3$PO$_4$, Na$_2$HPO$_4$, K$_2$HPO$_4$, NaH$_2$PO$_4$, KH$_2$PO$_4$, Na$_2$CO$_3$, K$_2$CO$_3$, NaHCO$_3$, and KHCO$_3$.

According to a further preferred embodiment, when the iodinating system comprises copper and thereby at least phosphoric acid, carbonic acid, and/or ions thereof, the phosphoric acid, carbonic acid, or ions thereof (e.g. when such component of the iodinating system is NaHCO$_3$) is comprised in amount of 0.01 M or higher, more preferably of 0.1 M or higher, within the reaction mixture of step c).

The components of the iodinating systems are commercially available, and can thus be obtained accordingly. Alternatively, the components of the iodinating systems can be prepared according to known methods. For example, Ag$_2$O can be obtained according to the method disclosed in Example 2 below.

Step c) of the process of the invention provides the 2,4,6-triiodophenol, as well as a precipitate of the element of group 11 with iodide ions, such as AgI and/or of CuI (based on the selected iodinating system). Indeed, part of the iodine deriving from I$_2$ is used to triiodinate the phenol, and part reacts with the free element of group 11, such as free Ag$^+$ and/or free copper ions to form AgI and/or CuI, respectively. This is particularly useful i.a. for two reasons, namely (i) because eventual excess of the iodinating species does not have to be treated according to conventional methods, as for instance by the addition of suitable amounts of alkali iodide, for example KI, to form the KI$_3$ complex, or by the addition of sodium sulphite or bisulfite, to remove such iodinating species from the mixture; and (ii) because the components of the iodinating system that have not participated in the triiodination reaction can be recovered from the precipitate of the element of group 11 with iodide ions, such as AgI and/or CuI salts, and can be re-used for further iodinations e.g. according to step c) of the process of the invention.

In view of the above, according to a preferred embodiment, when the iodinating system comprises silver, the process further comprises the following step:

d) converting at least part of AgI that is generated during and/or after step c) to I$_2$ and an oxide or a salt of silver different than AgI.

According to the embodiment comprising step d), the process of the invention has the further advantage of recovering the unreacted components of the iodinating system, such as the oxide or salt of silver and I2, thus improving the cost efficiency of the process itself. The recovered iodinating system can indeed be used for further reactions according to step c) of the process of the invention.

In particular, when the iodinating system comprises silver, step d) can be carried for example by:

d1) separating, e.g. by filtering out, AgI that is generated during and/or after step c) from the reaction mixture of step c);

d2) mixing the separated AgI with water or an aqueous solution to form a suspension;

d3) treating the suspension with reducing agents, preferably with hydrazine or NaBH$_4$, and optionally treating the suspension with sunlight, e.g. by exposing the suspension to sunlight preferably from 1 to 3 hours, to obtain suspended silver particles (Ag) within a solution comprising I$^-$;

d4) separating the silver particles from the solution comprising I$^-$;

d5) treating the silver particles with an oxidizing agent, such as HNO$_3$, to obtain AgNO$_3$; and d6) treating the solution comprising I$^-$ with an oxidizing agent to oxidize I$^-$ to I$_2$;

wherein steps d5) and d6) can be carried out in any order.

Step d5) can be carried out for example by mixing the separated silver particles Ag with an acidic solution comprising NO$_3^-$, such as a concentrated HNO$_3$ solution (at least 50% w/w, preferably 65% w/w concentration).

Step d6) can be carried out for example by mixing the solution comprising I$^-$ with a solution of KIO$_3$ (preferably, with the ratio of I$^-$ to KIO$_3$ being 5:1), or with a solution of HIO$_3$, for example as disclosed in WO 2011/154500, preferably under acidic conditions.

According to a preferred embodiment, when the iodinating system comprises copper, the process further comprises the following step:

e) converting at least part of CuI that is generated during and/or after step c) to $I_2$ and an oxide or a salt of copper different than CuI.

According to the embodiment comprising step e), the process of the invention has the further advantage of recovering the unreacted components of the iodinating system, such as the oxide or salt of copper and 12, thus improving the cost efficiency of the process itself. The recovered iodinating system can thereby be used for further reactions according to step c) of the process of the invention.

In particular, when the iodinating system comprises copper, step e) can be carried out for example by:

e1) separating, e.g. by filtering out, CuI that is generated during and/or after step c) from the reaction mixture of step c);

e2) mixing the separated CuI with a basic aqueous solution, for example a solution of NaOH, to obtain a solution comprising $I^-$ and precipitate $Cu(OH)_2$;

e3) separating, e.g. by filtering out, $Cu(OH)_2$ from the solution comprising $I^-$;

e4) mixing the filtrate $Cu(OH)_2$ to an acidic solution comprising $SO_4^{2-}$ to form $CuSO_4$; and e5) treating the solution comprising $I^-$ with an oxidizing agent to oxidize $I^-$ to $I_2$; wherein steps e4) and e5) can be carried out in any order.

Step e5) can be carried out for example by mixing the solution comprising $I^-$ with a solution of $KIO_3$ (preferably, with the ratio of $I^-$ to $KIO_3$ being 5:1), or with a solution of $HIO_3$, for example as disclosed in WO 2011/154500, preferably under acidic conditions.

Experimental Section

Material and Methods

Compound 1, used herein as the starting material of the process of the invention, is known and may be prepared according to the known methods. For a general reference to Compound 1 see, for instance, WO 88/09328, WO 97/05097 and WO 00/32561.

Any other reactant and/or solvent employed in the instant process is known and readily available. If they are not commercially available per se, they may be prepared according to known methods in literature.

Experimental setup of the HPLC-ESI-MS measurements
HPLC system: Agilent 1260 Infinity II HPLC instrument equipped with quaternary pump, degasser, autosampler, PDA and MS detector (LCQ Deca XP-Plus—Thermo Finnigan);
Stationary phase: Zorbax SB C18 (4.5 mm×150 mm-3.5 µm) Zorbax—art. 863953-902;
Mobile phase: 99% $NH_4OAc$ (10 mM, pH=4.6)/1% MeOH;
Elution: Isocratic;
Flow: 1.5 mL/min;
Temperature: 35° C.;
Detection: DAD at 210, 254, 300, 320 and 340 nm;
Injection volume: 10 µL;
Sample concentration: 0.3 mM Compound 1/Compound 1 Mono-iodinated/Compound 1 Di-Iodinated/Compound 2;
Stop time: 32 min;
Retention time about 2-10 min.

Experimental Setup of the $^1H$ NMR Spectroscopy Measurements $^1H$ NMR measurements were performed with a Bruker DRX 400 (9.4 T) spectrometer equipped with a Bruker VT-1000 thermocontroller (298 K) and a BB inverse z gradient probe (5 mm). $^1H$ NMR spectra of the samples were recorded by using standard Bruker Excitation Sculpting pulse sequence. Samples were prepared in $H_2O$ (a capillary with D20 was used for lock). The $^1H$ NMR spectra were analysed with TOPSPIN version 3.5 (Bruker) software.

Example 1 (Comparative)—Iodination of Compound 1 with $I_2$ at pH 7.5 and 25° C. (without Iodinating System)

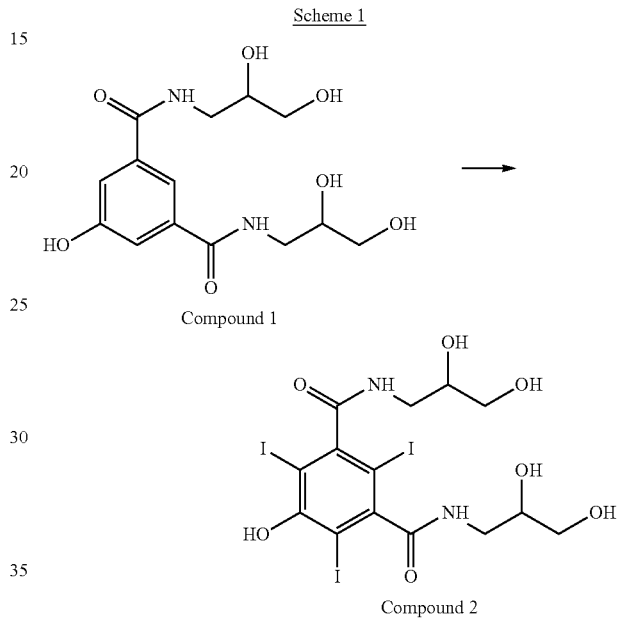

Scheme 1

Compound 1

Compound 2

A 25 mL 0.3 mM Compound 1 (Bracco Imaging) solution was prepared by dissolving 2.5 mg of Compound 1 (7.6 µmol) in 25 mL air-free distilled water. The reaction was started by addition of 5.6 mg of $I_2$ (Sigma, 22 µmol) to 20 mL of the 0.3 mM Compound 1 solution. The pH of the reaction was adjusted to 7.5 by stepwise addition of a solution of NaOH. The reaction was kept at 25° C. and stirred at 120 rpm.

To monitor the reaction, 1 mL solution samples were withdrawn time by time, and were analyzed by HPLC-ESI-MS and by $^1H$ NMR spectroscopy according to the experimental setups disclosed above. The 1 mL solution samples were filtered through a 0.45 µm syringe filter and mixed with 1.4 mg $Na_2SO_3$ (Sigma, 11 µmol) in order to quench the reaction by the reduction of the unreacted $I_2$ to $I^-$ anion.

The HPLC chromatogram of the sample gathered at 120 min reaction time obtained according to the present example shows the presence of Compound 1, and of the mono- and di-iodinated derivatives. The $^1H$ NMR spectra confirms this, as the signals of Compound 1, and of the mono- and di-iodinated derivatives, are still clearly visible at 114.3 min reaction time. Accordingly, the results of the HPLC measurements and NMR studies show that Example 1 (Comparative) provides partial, and thus incomplete, triiodination of Compound 1 within 2 hours, even in the presence of 3.7-fold excess of 12.

By taking into account the integral values of the aromatic protons of Compound 1, Compound 1 mono- and di-iodinated in the $^1H$ NMR spectra, the amount of Compound 2 formed in the iodination reaction of Example 1 (Comparative) was calculated by considering the total concentration of Compound 1 ([Compound 1]$_t$=[Compound 1]+[Compound 1 mono-I]+[Compound 1 di-I]+[Compound 2]=0.3 mM). The amount of Compound 1 as a function of time during the reaction of Example 1 (Comparative) is shown in FIG. 1 as diamond (◇). According to these data included in FIG. 1, the iodination of Example 1 (Comparative) provides a conversion of Compound 1 to Compound 2 of about 70% in 2 hours.

Example 2—Iodination of Compound 1 with $Ag_2O/I_2$ at pH 7.5 and 25° C.

A reaction according to Scheme 1 above was conducted as follows. Solid $Ag_2O$ was prepared by the addition of 40 mg NaOH (Sigma, 1 mmol) into 10 mL 0.1 M $AgNO_3$ solution (Sigma, 1 mmol). The brown $Ag_2O$ precipitate was filtered off by Buchner funnel, and washed four times with distilled water. The brown $Ag_2O$ precipitate was then dried for a night at reduced pressure to obtain 100 mg of $Ag_2O$ (0.43 mmol, yield: 86%). A 0.3 mM solution of Compound 1 was prepared by dissolving 2.5 mg of Compound 1 (7.6 μmol) in 25 mL of air-free distilled water. The iodinating reaction was started by addition of 5.6 mg $I_2$ (Sigma, 22 μmol) and 2.5 mg $Ag_2O$ (11 μmol) to 20 mL of the 0.3 mM Compound 1 solution. The pH of the reaction was adjusted to 7.5 by stepwise addition of a solution of $NH_3$. The reaction was kept at 25° C. and stirred at 120 rpm.

To monitor the reaction, 1 mL solution samples were withdrawn time by time and were analyzed by HPLC-ESI-MS and by $^1$H NMR spectroscopy according to the experimental setups disclosed above. The 1 mL solution samples were filtered through a 0.45 μm syringe filter and mixed with 1.4 mg $Na_2SO_3$ (Sigma, 11 μmol) in order to quench the reaction by the reduction of the unreacted $I_2$ to $I^-$ anion.

The HPLC chromatogram of the sample obtained at 45 min reaction time of the iodination of the present example shows the substantial absence of signals of Compound 1, and of the mono- and di-iodinated derivatives, thereby confirming the substantial complete (yield >90%) formation of Compound 2 within 45 min at pH=7.5 and 25° C. This substantially complete formation (yield >90%) was confirmed by the ESI-MS and the $^1$H NMR spectra. The $^1$H NMR spectra further confirm the final completion (yield about 99%) after about 80 min reaction time.

Similarly to Example 1 (Comparative), the amount of Compound 2 formed in the iodination reaction of Example 2 was calculated by considering the total concentration of Compound 1 and is shown in FIG. 1 as triangle (Δ).

Example 3—Iodination of Compound 1 with $CuSO_4/NaHCO_3/I_2$ at pH 7.5 and 25° C.

A reaction according to Scheme 1 above was conducted as follows. A 0.3 mM solution of Compound 1 was prepared by dissolving 2.5 mg Compound 1 (7.6 μmol) in 25 mL air-free distilled water. The tri-iodination reaction was started by addition of 5.6 mg $I_2$ (Sigma, 22 μmol), 5.5 mg $CuSO_4$+$5H_2O$ (Sigma, 22 μmol) and 336 mg $NaHCO_3$ (Sigma, 4 mmol) to 20 mL of the 0.3 mM Compound 1 solution. The pH of the reaction was adjusted to 7.5 by stepwise addition of a solution of NaOH. The reaction was kept at 25° C. and stirred at 120 rpm.

To monitor the reaction, 1 mL solution samples were withdrawn time by time and were analyzed by $^1$H NMR spectroscopy according to the experimental setups disclosed above. The 1 mL solution samples were filtered through a 0.45 μm syringe filter and mixed with 1.4 mg $Na_2SO_3$ (Sigma, 11 μmol) in order to quench the reaction by the reduction of the unreacted $I_2$ to $I^-$ anion.

$^1$H NMR spectra for the present example confirm the at least substantially complete tri-iodination of Compound 1 at 86 min.

Similarly to Example 1 (Comparative), the amount of Compound 2 formed in the iodination reaction of Example 3 was calculated by considering the total concentration of Compound 1 and is shown in FIG. 1 as circle (•).

Example 4—Direct Comparison Between Example 1 (Comparative), Example 2 and Example 3

By taking into account the integral values of the aromatic protons of Compound 1, of Compound 1 mono-iodinated, and Compound 1 di-iodinated in the $^1$H NMR spectra obtained for Examples 1 (Comparative), 2 and 3, the amounts of Compound 2 ("Tri-I" in FIG. 1) formed in the iodination reactions of such Examples have been calculated by considering the total concentration of Compound 1 ([Compound 1]$_t$=[Compound 1]+[Compound 1 Mono-I]+[Compound 1 Di-I]+[Compound 2]=0.3 mM, i.e. 3×10$^{-4}$ mol/dm$^3$ in FIG. 1). These amounts are reported in FIG. 1 (Example 1 (Comparative): diamond ◇; Example 2: triangle Δ; and Example 3: circle •).

FIG. 1 clearly shows the improvement in reaction time and completeness of the process of the invention when compared to a process not according to the invention.

Example 5—Recovery of the Iodinating System Comprising Silver from AgI 46.95 mg of AgI (0.2 mmol) obtained as by-product by the iodination process of the invention, e.g. according to Example 2, was filtered out from the reaction mixture after substantial completion thereof. AgI precipitate was then washed 3 times with 5 mL bidistilled water and centrifuged (6000 rpm, 10 min). 80 mg $NaBH_4$ (80 mg, 2.1 mmol) (Sigma) was added to AgI precipitate suspended in 3 mL bidistilled water. Suspension was stirred for 20 min in atmospheric condition. Elementary Ag formed by the reduction of AgI precipitate was washed 3 times with 5 mL bidistilled water and centrifuged (6000 rpm, 10 min). After the centrifugations the supernatant comprising $I^-$ ions (in particular, NaI) released from AgI precipitate was collected and 50 mL stock solution was prepared with bidistilled water. After the washing procedure the retained elementary Ag was dissolved in 3 mL 65% ultrapure $HNO_3$ (Sigma). The acid excess of the resulting $AgNO_3$ solution was evaporated in atmospheric condition. After the evaporation of the acid excess, 20 mL stock solution was prepared by dissolving $AgNO_3$ in 0.1 M $HNO_3$.

$I_2$ can be obtained from the supernatant comprising $I^-$ ions for example by treating it with an oxidating agent, such as $HIO_3$ or $KIO_3$, e.g. as disclosed in step d6) or e5) of the invention.

Concentration of the $AgNO_3$ and NaI solution was determined by potentiometric titration with standardized 0.015 M KI solution. For potentiometric measurements and titrations, a Metrohm 888 Titrando titration workstation equipped with Metrohm-6.0502.160 $I^-$ selective electrode and Metrohm-6.0750.100 double junction reference electrode was used. Potentiometric measurements were carried out at constant pH (a: pH=7.4, 0.01 M HEPES; b: pH=1.7, 0.02 M $HNO_3$) and constant ionic strength (0.15 M $NaNO_3$) in 10 mL samples at 25° C. Solutions were stirred and continuously purged with $N_2$. For the calculation of the [NaI] recovered from AgI, the potentiometric system was calibrated with standardized 0.015 M KI solution at pH=7.4 and 25° C. in 0.01 M HPES solution. For this experiment 10 mL aqueous solution prepared with 0.01 M HEPES and 0.15 M $NaNO_3$ at pH=7.4 and 25° C. was titrated with standardized 0.015 M KI solution. The slope (102.3%) and $pI_0$ (6.40) values calculated from E (mV) vs. pI data pairs of the calibration have been used to calculate the [$I^-$] of the NaI solution.

To determine the concentration of the $AgNO_3$ recovered from AgI, the potentiometric system was also calibrated with standardized 0.015 M KI solution at acidic condition in order to avoid the precipitation of $Ag^+$ ion in the form of $Ag_2O$. For this experiment, 10 mL aqueous solution prepared with 0.02 M $HNO_3$ and 0.15 M $NaNO_3$ at 25° C. was titrated with 0.015 M KI solution. The slope (101.8%) and $pI_0$ (6.43) values calculated from E (mV) vs. pI data pairs of the calibration have been used to calculate the pI values in the titration experiment. To calculate the concentration of $AgNO_3$ recovered from AgI, $AgNO_3$ solution (10 mL, 0.02 M $HNO_3$, 0.15 M $NaNO_3$, 25° C.) was titrated with standardized 0.015 M KI solution. The pI values calculated from measured E(mV) as a function of $V_{KI}$ (mL) have been used to calculate the concentration of the $AgNO_3$ recovered from AgI.

Based on the potentiometric experiments the concentration of the 50 mL NaI and 20 mL $AgNO_3$ stock solutions obtained from the recovery of AgI precipitate was found to be 0.00361 and 0.009773 mol/$dm^3$ ($I^-$: 0.181 mmol; $Ag^+$: 0.196 mmol), respectively. By considering the amount of AgI precipitate (0.2 mmol), the yield of the $I^-$ and $Ag^+$ recovery was found to be 91 and 98%, respectively.

The invention claimed is:

1. A process for the preparation of a 2,4,6-triiodophenol of formula (II), or a salt thereof,

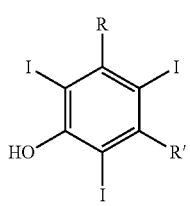

Formula (II)

wherein R and R' represent, independently from one another, a moiety selected from the group consisting of hydrogen, —$COOR_1$, and —$CONR_1R_2$;
wherein $R_1$ and $R_2$ represent, independently from one another, hydrogen or a $C_1$-$C_6$ alkyl group optionally substituted by one or more groups selected from hydroxyl (—OH), $C_1$-$C_6$ alkoxy, and $C_1$-$C_6$ hydroxyalkoxy;
comprising the following steps:
a) providing a phenol of formula (I), or a salt thereof

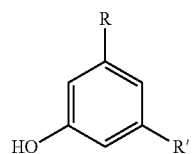

Formula (I)

wherein R and R' have the same meaning provided above;
b) providing an iodinating system comprising $I_2$, and at least an oxide or a salt of an element of group 11 of the periodic table, provided that when the element of group 11 is copper, the iodinating system further comprises phosphoric acid, carbonic acid, and/or ions thereof,
c) reacting said phenol of step a) and said iodinating system of step b) in an aqueous medium having a pH comprised in the range of 7.0 to 9.0, to obtain the 2,4,6-triiodophenol of formula (II).

2. The process according to claim 1, wherein the element of group 11 is silver or copper.

3. The process according to claim 2, wherein the iodinating system comprises a silver oxide and/or a salt of copper and $I_2$, provided that when the iodinating system comprises said salt of copper, the iodinating system further comprises at least phosphoric acid, carbonic acid, and/or ions thereof.

4. The process according to claim 1, wherein when the element of group 11 is copper, the iodinating system further comprises at least an ion of phosphoric acid or carbonic acid selected from the group consisting of phosphate ($PO_4^{3-}$), monohydrogen phosphate ($HPO_4^{2-}$), dihydrogen phosphate ($H_2PO_4^-$), carbonate ($CO_3^{2-}$), and bicarbonate ($HCO_3^-$).

5. The process according to claim 1, wherein the iodinating system is selected from the group consisting of $Ag_2O/I_2$, $I_2/CuSO_4/NaHCO_3$, and mixtures thereof.

6. The process according to claim 1, wherein for both formulae (I) and (II), R and R' represent, independently from one another, a —$COOR_1$ or a —$CONR_1R_2$ moiety, wherein $R_1$ and $R_2$, independently from one another, represent hydrogen or a $C_1$-$C_4$ alkyl group optionally substituted by from one to three hydroxyl (—OH).

7. The process according to claim 6, wherein the phenol is N,N'-bis[2,3-dihydroxypropyl]-5-hydroxybenzene-1,3-dicarboxamide (Compound 1),

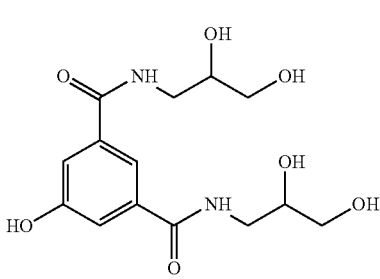

Compound 1 and the 2,4,6-triiodophenol is N,N'-bis[2,3-dihydroxypropyl]-5-hydroxy-2,4,6-triiodobenzene-1,3-dicarboxamide (Compound 2)

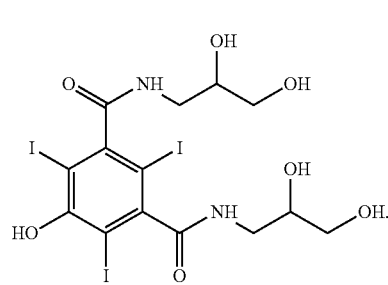

Compound 2

8. The process according to claim 1, wherein step c) is carried out with a ratio of at least three moles of $I_2$ per mole of phenol.

9. The process according to claim 1, wherein, when the iodinating system comprises silver, the molar ratio between $I_2$ and silver is at least 4:1.

10. The process according to claim 1, wherein, when the iodinating system comprises copper, the molar ratio between $I_2$ and copper is comprised in the range of 1:0.8 to 1:3.

11. The process according to claim 1, wherein, when the iodinating system comprises copper and thereby at least phosphoric acid, carbonic acid, and/or ions thereof, the phosphoric acid, carbonic acid, and/or ions thereof are comprised in amount of 0.01 M or higher within the reaction mixture of step c).

12. The process according to claim 1, wherein, when the iodinating system comprises silver, the process further comprises the following step:
   d) converting at least part of AgI that is generated during and/or after step c) to $I_2$ and an oxide or a salt of silver different than AgI.

13. The process according to claim 1, wherein, when the iodinating system comprises copper, the process further comprises the following step:
   e) converting at least part of CuI that is generated during and/or after step c) to $I_2$ and an oxide or a salt of copper different than CuI.

14. The process according to claim 1, wherein the reaction of step c) is carried out by adjusting to and/or maintaining the temperature to 40° C. or lower.

15. The process according to claim 1, wherein the reaction of step c) is carried out for a time of less than 2 hours.

16. The process according to claim 1, wherein step c) is carried out with a molar ratio of $I_2$ to phenol comprised in the range of 3:1 to 4:1.

17. The process according to claim 1, wherein, when the iodinating system comprises silver, the molar ratio between $I_2$ and silver is comprised in the range of 4:1 to 1:1.

18. The process according to claim 1, wherein, when the iodinating system comprises copper, the molar ratio between $I_2$ and copper is 1:1.

19. The process according to claim 1, wherein, when the when the iodinating system comprises copper and thereby at least phosphoric acid, carbonic acid, and/or ions thereof, the phosphoric acid, carbonic acid, and/or ions thereof are comprised in amount of 0.1 M or higher within the reaction mixture of step c).

20. The process according to claim 1, wherein the reaction of step c) is carried out by adjusting to and/or maintaining the temperature to the range of 15° C. to 35° C.

* * * * *